US012332257B2

(12) United States Patent
Heydlauf

(10) Patent No.: US 12,332,257 B2
(45) Date of Patent: Jun. 17, 2025

(54) PREDICTIVE QUALITY CONTROL APPARATUS AND METHODS IN DIAGNOSTIC TESTING SYSTEMS

(71) Applicant: Siemens Healthcare Diagnostics Inc., Tarrytown, NY (US)

(72) Inventor: Michael Heydlauf, Cary, NC (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 965 days.

(21) Appl. No.: 16/961,982

(22) PCT Filed: Feb. 11, 2019

(86) PCT No.: PCT/US2019/017458
§ 371 (c)(1),
(2) Date: Jul. 14, 2020

(87) PCT Pub. No.: WO2019/177724
PCT Pub. Date: Sep. 19, 2019

(65) Prior Publication Data
US 2021/0081839 A1    Mar. 18, 2021

Related U.S. Application Data

(60) Provisional application No. 62/642,763, filed on Mar. 14, 2018.

(51) Int. Cl.
*G01N 35/00* (2006.01)
*G06N 5/04* (2023.01)
(Continued)

(52) U.S. Cl.
CPC ......... *G01N 35/00623* (2013.01); *G06N 5/04* (2013.01); *G06N 20/00* (2019.01); *G16H 40/40* (2018.01); *G01N 2035/00653* (2013.01)

(58) Field of Classification Search
CPC ....... G01N 35/00632; G01N 35/00613; G01N 35/00594; G01N 2035/00653; G06N 5/04; G06N 20/00; G16H 40/40
See application file for complete search history.

(56) References Cited

U.S. PATENT DOCUMENTS 5,695,718 A * 12/1997 Imai ................. G01N 35/00594
422/65
6,556,951 B1   4/2003 Deleo et al.
(Continued)

FOREIGN PATENT DOCUMENTS

| JP | 2006017600 A | 1/2006 | |
| JP | 2006164295 A | 6/2006 | |
| WO | WO-2018099859 A1 * | 6/2018 | ....... G01N 35/00613 |

OTHER PUBLICATIONS

Wikipedia: "Condition monitoring"; Feb. 1, 2018; pp. 1-7; XP055790532; URL: https://en.wikipedia.org/w/index.php?title=Condition monitoring&oldid=823474864 [retrieved on Mar. 26, 2021] / Jan. 2, 2018.

(Continued)

*Primary Examiner* — Manuel L Barbee

(57) ABSTRACT

Predictive quality control apparatus and methods for diagnostic testing systems may include a decision module that continually receives and correlates related data along with quality control results. The related data may include, but not be limited to, one or more of the number and type of tests previously performed by a diagnostic analyzer, analyzer temperature, vibration level, humidity level, atmospheric pressure, degree of water ionization, refrigerated storage temperature of components used by the diagnostic analyzer, reagent lot number, reagent lot expiration, and/or other sensor and/or externally-sourced data. The decision module may be trained with quality control results indicating acceptable and unacceptable analyzer operation along with the (Continued)

related data in order to recognize patterns that may indicate subsequent unacceptable analyzer operation. The predictive apparatus and methods may accordingly notify a user of potentially unacceptable analysis operation well before discovery of such by conventional quality control testing.

22 Claims, 3 Drawing Sheets

(51) Int. Cl.
*G06N 20/00* (2019.01)
*G16H 40/40* (2018.01)

(56) References Cited

U.S. PATENT DOCUMENTS

| | | | |
|---|---|---|---|
| 6,937,964 B2 | 8/2005 | Okuno et al. | |
| 6,984,527 B2 | 1/2006 | Miller | |
| 7,925,461 B2 | 4/2011 | Yamaguchi et al. | |
| 2005/0177345 A1 | 8/2005 | Okuno et al. | |
| 2008/0312893 A1 | 12/2008 | Denton | |
| 2009/0198450 A1* | 8/2009 | Fernandez | A61B 5/486 702/19 |
| 2012/0042214 A1 | 2/2012 | Jacobs et al. | |
| 2014/0288854 A1 | 9/2014 | Satomura et al. | |
| 2016/0339726 A1* | 11/2016 | Dugge | B41J 29/393 |
| 2017/0053091 A1 | 2/2017 | Holmes et al. | |
| 2017/0285624 A1* | 10/2017 | Lesher | G05B 19/41875 |
| 2020/0124576 A1* | 4/2020 | Kobold | G01N 30/88 |

OTHER PUBLICATIONS

International Search Report for PCT/US2019/017458 dated Apr. 19, 2019.

* cited by examiner

PREDICTIVE QUALITY CONTROL APPARATUS AND METHODS IN DIAGNOSTIC TESTING SYSTEMS

FIELD

This disclosure relates to methods and apparatus for predictive quality control in diagnostic testing systems.

BACKGROUND

In medical testing and processing, diagnostic analyzers may be used to test concentrations of certain constituents found in biological specimens, such as, e.g., blood, urine, cerebrospinal liquids, and like fluid samples. Such diagnostic analyzers may be complex and may perform hundreds or even thousands of diagnostic tests each day. In order to ensure that the results produced by a diagnostic analyzer are valid, quality control tests may be performed thereon using quality control samples that should produce expected results. Quality controls tests may be performed, for example, at the beginning of each shift, after a diagnostic analyzer is serviced or calibrated, when reagent lots are changed, after a certain period of time has elapsed, after a certain number of diagnostic tests have been performed, and/or whenever patient results seem inappropriate. If a quality control test does not produce the expected result, the diagnostic analyzer may be considered "out of control." That is, the diagnostic analyzer is operating unacceptably and all of the results produced by that diagnostic analyzer since the last successful quality control test may be questionable and may have to be rerun. Furthermore, because quality control tests are potentially expensive for a lab to perform (i.e., they consume reagent supplies and analyzer cycle time), performing more quality control tests may not be a desirable solution.

Accordingly, methods and apparatus that can improve quality control in diagnostic testing systems are sought.

SUMMARY

According to a first aspect, a quality control method is provided. The quality control method includes receiving, at a controller, analyzer results from a diagnostic analyzer in response to executing a quality control test; receiving, at the controller, data related to the diagnostic analyzer; analyzing, with a decision module executing in the controller, the analyzer results and the data related to the diagnostic analyzer; and sending, from the controller to a user interface, a message indicating that the diagnostic analyzer is operating acceptably now but subsequently may not continue to do so based on the analyzing by the decision module.

According to a second aspect, a quality control apparatus is provided. The quality control apparatus includes a diagnostic analyzer configured to perform one or more tests on biological specimens, a controller in electronic communication with the diagnostic analyzer, and a user interface coupled to the controller. The controller includes a communication interface configured to receive (1) analyzer results from the diagnostic analyzer in response to the diagnostic analyzer executing a quality control test, and (2) data related to the diagnostic analyzer. The controller also includes a decision module configured and operable to analyze the analyzer results and the data related to the diagnostic analyzer in order to determine whether the diagnostic analyzer is operating acceptably, unacceptably, or acceptably now but subsequently may not continue to do so.

Still other aspects, features, and advantages of the invention may be readily apparent from the following detailed description illustrating a number of example embodiments. This disclosure may also be capable of different embodiments, and its several details may be modified in various respects. Accordingly, this disclosure covers all modifications, equivalents, and alternatives falling within the scope of claims appended below.

DETAILED DESCRIPTION

In vitro diagnostic analyzers may rely on quality control tests to ensure that the results produced by the diagnostic analyzers are valid. A quality control test involves testing a quality control sample in the diagnostic analyzer and comparing the analyzer result with an expected result for that quality control sample. If a diagnostic analyzer does not produce the expected result from a quality control test, the diagnostic analyzer may be considered to be "out of control" and all of the results produced by that diagnostic analyzer since the last successful quality control test may now be called into question.

Figure 1:
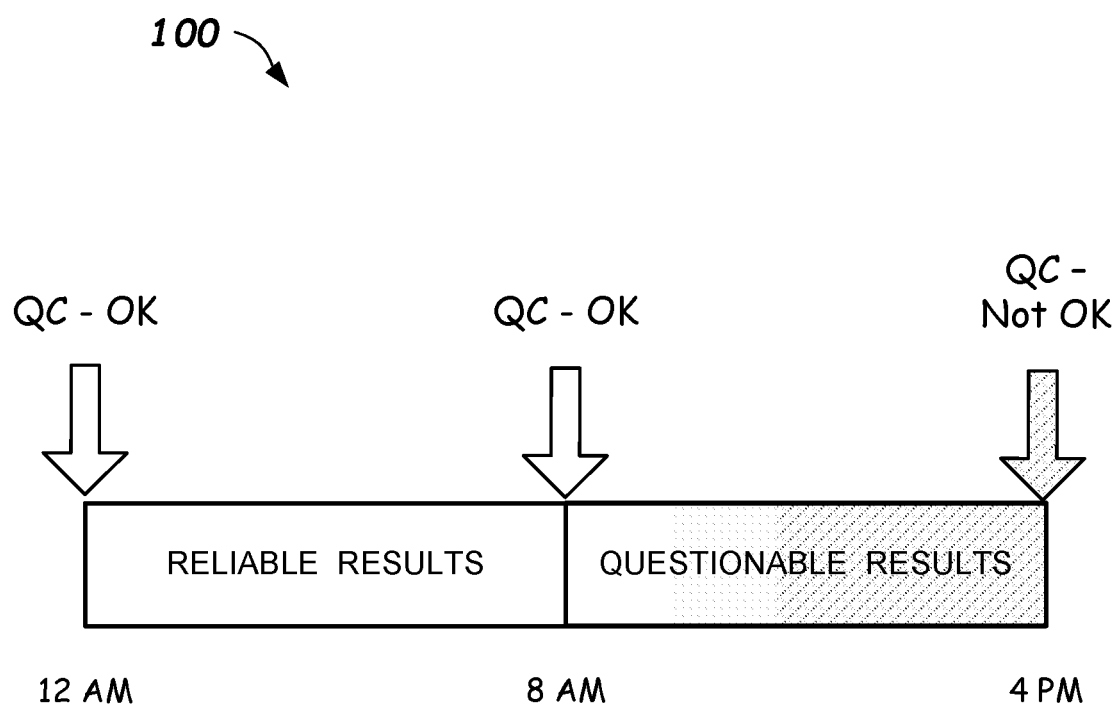
FIG. 1 illustrates a timeline of known quality control performed on a diagnostic analyzer.

For example, FIG. 1 shows a timeline 100 of operating a diagnostic analyzer. A first quality control test according to the prior art may be performed at, e.g., 12:00 AM that may indicate that the diagnostic analyzer is operating acceptably (i.e., the analyzer results correspond to the expected results of the first quality control test). A second quality control test according to the prior art may be performed at, e.g., 8:00 AM that may also indicate that the diagnostic analyzer is operating acceptably. This successful second quality control test may ensure that all of the analyzer results produced between 12:00 AM and 8:00 AM are reliable and valid. However, a third quality control test according to the prior art may be performed at 4:00 PM that may indicate that the diagnostic analyzer is not operating acceptably (i.e., the analyzer results do not correspond to the expected results of the third quality control test). Consequently, some or all of the analyzer results produced between 8:00 AM and 4:00 PM may not be reliable and/or valid. Thousands of diagnostic tests may have been performed between the second and third quality control tests. Thus, a potentially large amount of rework and associated cost (particularly in terms of manpower and reagent supplies used in the testing of biological specimens) may be incurred to rerun or re-validate those analyzer results.

In view of the foregoing, one or more embodiments of the disclosure provide predictive quality control methods and apparatus configured and operable to predict when a diagnostic analyzer may no longer operate acceptably. These methods and apparatus may obtain and analyze other data related to the operation of the diagnostic analyzer on a continual basis in addition to comparing analyzer results from a quality control test with expected results of the quality control test. The analysis of the related data may indicate that although the diagnostic analyzer is currently operating acceptably (i.e., the analyzer results from the quality control test correspond to the expected results), the diagnostic analyzer may not continue to operate acceptably in the near future. In some embodiments, the analysis may provide an estimated time frame within which the diagnostic analyzer may be "out of control." Thus, referring to FIG. 1, performing predictive quality control according to embodiments of the disclosure may indicate based on the continual receipt and analysis of related data that while the diagnostic analyzer is currently operating acceptably, it may not continue to do so within, e.g., the next 2-4 hours. Such an indication, which may occur at any time during or between quality control tests, may allow a user of the diagnostic analyzer to initiate remedial procedures before continuing with possibly thousands of diagnostic tests, thus saving time, reducing costs, and possibly improving patient safety by avoiding the production of possibly invalid analyzer results. Advantageously, the predictive quality control methods and apparatus according to embodiments may further save time and reduce costs by allowing quality control tests to be performed less often. That is, because the predictive quality control methods and apparatus according to embodiments are configured to alert a user of possibly unacceptable operation before such unacceptable operation actually occurs, a diagnostic analyzer may be allowed to operate for longer periods of time between quality control tests.

These and other aspects and features of embodiments of the disclosure will be described with reference to FIGS. 2 and 3.

Figure 2:
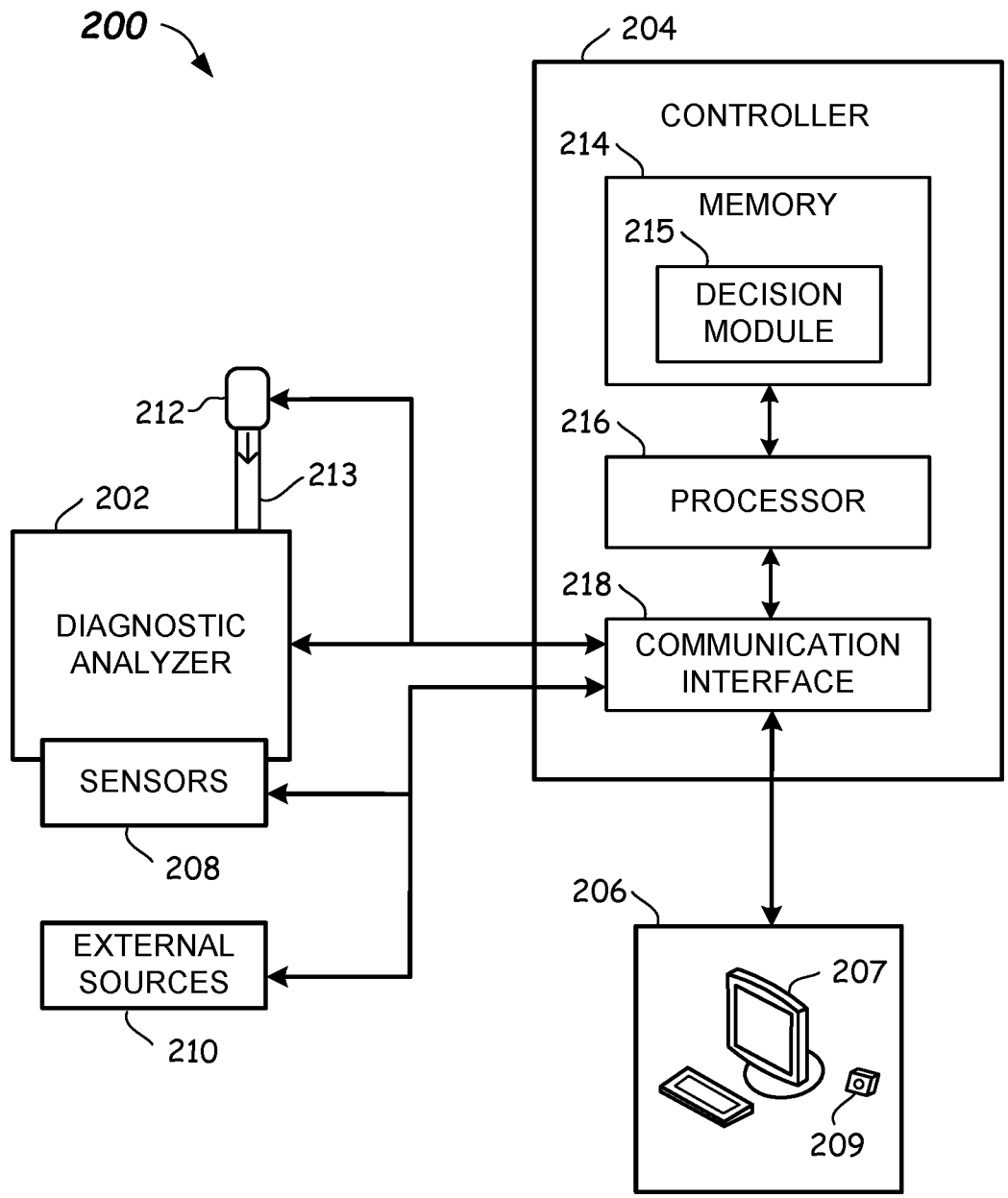
FIG. 2 illustrates a schematic block diagram of a quality control apparatus according to embodiments.

FIG. 2 illustrates a quality control apparatus 200 according to embodiments. Quality control apparatus 200 may include a diagnostic analyzer 202, a controller 204, a user interface 206, one or more sensors 208, optional external data sources 210, and quality control sample specimens 212. Diagnostic analyzer 202 may be configured to perform one or more diagnostic tests and/or analyses on biological specimens. Quality control apparatus 200 is configured and operative to predictively indicate when operation of diagnostic analyzer 202 may no longer be acceptable. In other words, quality control apparatus 200 is configured and operative to predictively indicate when analyzer results from diagnostic analyzer 202 may no longer be valid or reliable.

Controller 204, which may be any suitable computer device, may include a memory 214 (e.g., RAM, ROM, or other) configured to store programming instructions, test result data, and/or other information/data. Controller 204 may also include a processor 216 (e.g., a CPU, microprocessor, or the like) configured to execute programming instructions in connection with the operation of quality control apparatus 200, including the performing of quality control tests on diagnostic analyzer 202. Controller 204 may further include a communication interface 218 via which controller 204 may be coupled to and in electronic communication with diagnostic analyzer 202, user interface 206, sensors 208, external sources 210, and apparatus 213 for transporting a quality control sample specimen 212 into diagnostic analyzer 202. In some embodiments, communication interface 218 may enable communication with a network (not shown) coupled between controller 204 and one or more of the other components of quality control apparatus 200. The network may include, e.g., a local area network (LAN), a wireless local area network (WLAN), a power line communication (PLC) network, or the like.

Communication interface 218 may be configured to receive analyzer results from diagnostic analyzer 202 in response to diagnostic analyzer 202 executing a quality control test. Communication interface 218 may also be configured to receive data related to diagnostic analyzer 202 obtained from sensors 208 and/or external sources 210.

The data related to diagnostic analyzer 202 may be provided by the one or more sensors 208 and/or the one or more external sources 210 on a continual basis. External sources 210 may include manually provided data. Sensors 208 (e.g., thermometers, bar code readers, barometers, etc.) may be internal and/or external to diagnostic analyzer 202 and may be configured to provide various readings or measurements of at least some of the data related to the operation of diagnostic analyzer 202. This related data may include, but not be limited to, one or more of the following: a sequence, number, or type of tests previously performed by diagnostic analyzer 202; internal temperature of diagnostic analyzer 202; level of internal vibrations of diagnostic analyzer 202; humidity level; atmospheric pressure; degree of water ionization; refrigerated storage temperature of reagents and/or other specimen sample additives; reagent lot number; reagent lot expiration date; and/or onboard stability expiration date. Other types of data related to the operation of diagnostic analyzer 202 may additionally or alternatively be included.

Controller 204 may also include a decision module 215 stored in memory 214 and executable by processor 216. The decision module 215 may be configured and operable to compare the analyzer results with expected results from a quality control test. The decision module 215 may also be configured and operable to analyze the analyzer results and the data related to diagnostic analyzer 202 to determine whether diagnostic analyzer 202 is operating acceptably, unacceptably, or acceptably now but subsequently may not. The decision module 215 may include an artificial intelligence-driven model trained to identify patterns in the data related to diagnostic analyzer 202 that may indicate subsequent unacceptable diagnostic analyzer operation.

For example, quality control data stored in memory 214 may indicate that acceptable analyzer operation (i.e., analyzer results corresponding to expected results of a quality control test) may be associated with related data having a first set or range of one or more values, while unacceptable analyzer operation (i.e., analyzer results not corresponding to expected results of a quality control test) may be associated with related data having a second set or range of one or more values. Accordingly, in response to receiving related data wherein at least some related data has one or more values between the first and second sets or ranges of values, decision module 215 may determine that diagnostic analyzer 202 may not continue operating acceptably and may prompt controller 204 to issue a warning message to user interface 206. In some embodiments, decision module 215 may provide a time frame (e.g., within the next 3-5 hours) during which unacceptable analyzer operation may be expected. This time frame may be based on, e.g., how quickly the one or more values between the first and second sets or ranges of values may be moving toward the second set or range of values.

User interface 206 may include a display device 207 configured to display messages received from controller 204. The messages may indicate that diagnostic analyzer 202 is operating acceptably, unacceptably, or acceptably now but subsequently may not. In some embodiments, user interface 206 may also include an audible warning device 209 that may be configured to activate in response to a message sent from controller 204 indicating that diagnostic analyzer 202 is operating either unacceptably or acceptably now but subsequently may not.

Figure 3:
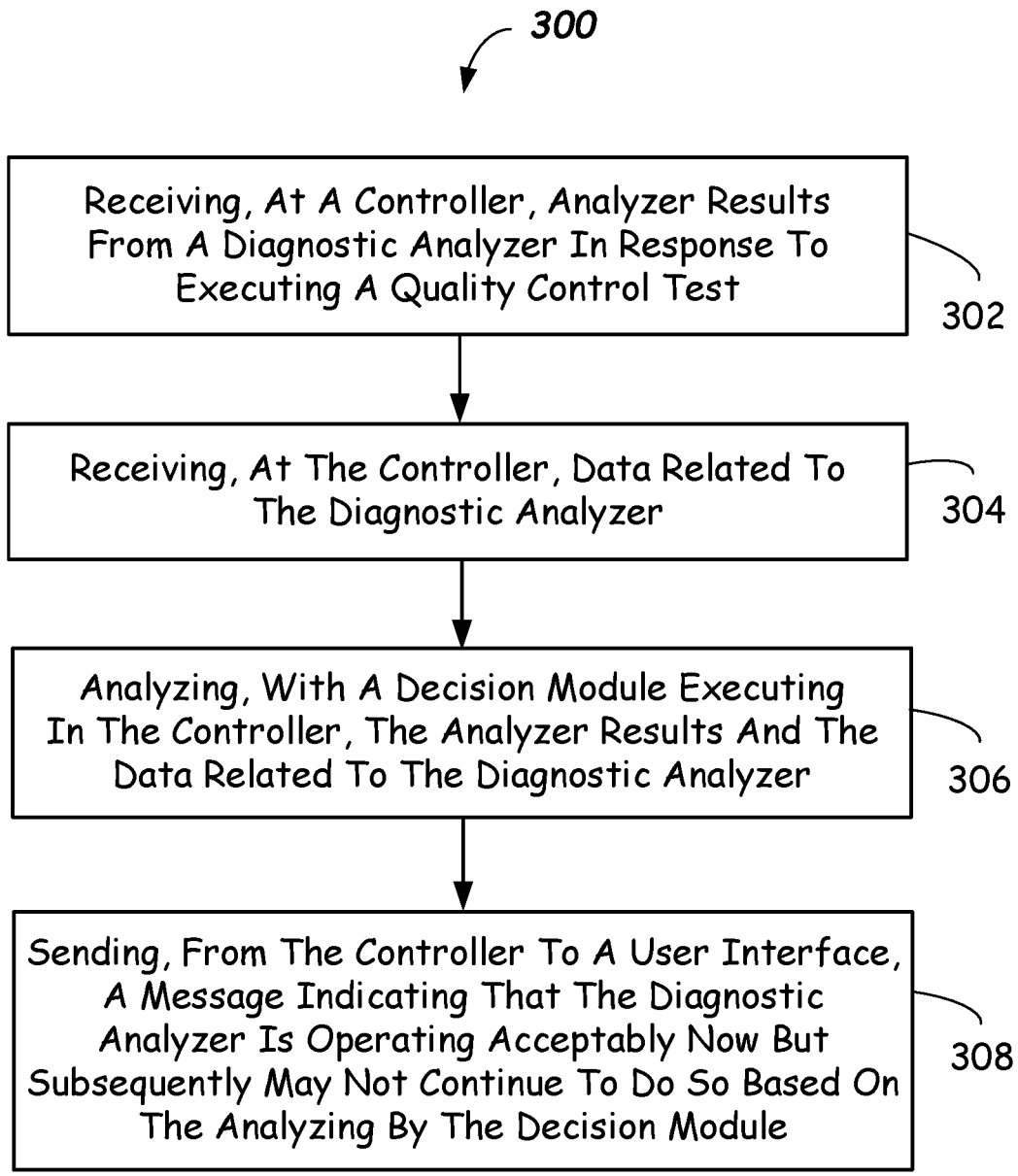
FIG. 3 illustrates a flowchart of a quality control method according to embodiments.

FIG. 3 shows a quality control method 300 according to embodiments. Method 300 may be carried out by, e.g., controller 204 and diagnostic analyzer 202 of quality control apparatus 200. Method 300 may include, in process block 302, receiving, at a controller, analyzer results from a diagnostic analyzer in response to executing a quality control test. For example, referring to FIG. 2, controller 204 may initiate a quality control test by directing a quality control sample specimen 212 to be transported to diagnostic analyzer 202 for a quality control test. Controller 204 may then receive the analyzer results of that quality control test from diagnostic analyzer 202.

Method 300 may also include, in process block 304, receiving, at the controller, data related to the diagnostic analyzer. For example, again referring to FIG. 2, sensors 208 and/or external sources 210 may continually provide to controller 204 related data, such as, e.g., one or more of previous testing information, reagent information, equipment status, and/or environmental readings or measurements (e.g., temperature, humidity, vibration, atmospheric pressure, etc.).

At process block 306, method 300 may include analyzing, with a decision module executing in the controller, the analyzer results and the data related to the diagnostic analyzer. For example, decision module 215 may compare the analyzer results with the expected results for the tested quality control sample specimen 212 and may further analyze the data related to the diagnostic analyzer in view of previously stored data related to diagnostic analyzer 202 in order to determine the operational status of diagnostic analyzer 202 and predict subsequent operational status of diagnostic analyzer 202.

And at process block 308, method 300 may include sending, from the controller to a user interface, a message indicating that the diagnostic analyzer is operating acceptably now but subsequently may not continue to do so based on the analyzing in process block 306. For example, controller 204 may send a message to user interface 206 indicating the operational status of diagnostic analyzer 202. Controller 204 additionally or alternatively may activate audible warning device 209 in response to sending a message to user interface 206 indicating that diagnostic analyzer 202 is operating either unacceptably or acceptably now but subsequently may not continue to do so.

While specific apparatus and methods have been shown by way of example embodiments herein, it should be understood that other and different embodiments are possible. This disclosure is intended to cover all modifications, equivalents, and alternatives falling within the scope of the following claims.

What is claimed is:

1. A quality control method, comprising:
   receiving, at a controller, a quality control test result from a diagnostic analyzer in response to executing a quality control test;
   receiving continually, at the controller, before a next quality control test, a plurality of data values related to the diagnostic analyzer, each data value associated with a first set or range of one or more values indicating acceptable analyzer operation and a second set or range of one or more values indicating unacceptable analyzer operation;
   analyzing, with a decision module executing in the controller, the quality control test result and the data values related to the diagnostic analyzer to determine whether the quality control test result corresponds with an expected quality control test result and whether each of the data values corresponds with its associated first set or range of one or more values or its associated second set or range of one or more values; and
   sending, from the controller to a user interface, a message indicating that the diagnostic analyzer is operating acceptably now and analyzer results received from the diagnostic analyzer are valid but the diagnostic analyzer subsequently may not continue to operate acceptably and subsequent analyzer results may not be valid in response to the decision module determining that the quality control test result corresponds with the expected quality control test result and at least one of the data values is between the first and second sets or ranges of one or more values associated with that at least one of the data values.

2. The quality control method of claim 1, wherein the decision module comprises an artificial intelligence-driven model trained to identify patterns in the data values related to the diagnostic analyzer that indicate subsequent unacceptable diagnostic analyzer operation.

3. The quality control method of claim 1, wherein the data values related to the diagnostic analyzer comprise data values received from one or more thermometers, bar code readers, and barometers.

4. The quality control method of claim 1, wherein the data values related to the diagnostic analyzer comprise one or more of:
   a sequence, number, or type of tests previously performed by the automated analyzer;
   internal temperature reading of the diagnostic analyzer;
   internal vibration level of the diagnostic analyzer;
   humidity level; and
   atmospheric pressure reading.

5. The quality control method of claim 1, wherein the data values related to the diagnostic analyzer comprise one or more of:
   degree of water ionization;
   refrigerated storage temperature reading;
   reagent lot number;
   reagent lot expiration date; and
   onboard stability expiration date.

6. The quality control method of claim 1, further comprising predicting a time frame during which operation of the diagnostic analyzer becomes unacceptable.

7. The quality control method of claim 6, wherein:
   the predicting a time frame comprises predicting the time frame during which operation of the diagnostic analyzer becomes unacceptable based on how quickly continually received data values related to the diagnostic analyzer have one or more values moving from the first set or range of one or more values toward the second set or range of one or more values.

8. The quality control method of claim 1, wherein the sending, from the controller to a user interface, the message occurs between quality control tests.

9. The quality control method of claim 1, wherein the analyzing comprises analyzing the data values related to the diagnostic analyzer with previously stored data values related to the diagnostic analyzer to predict subsequent unacceptable diagnostic analyzer operation.

10. The quality control method of claim 1, wherein the user interface includes a display device.

11. The quality control method of claim 1, further comprising activating an audible warning device in the user interface in response to the controller sending the message indicating that the diagnostic analyzer is operating acceptably now but subsequently may not continue to operate acceptably.

12. A quality control method, comprising:
receiving, at a controller, a quality control test result from a diagnostic analyzer in response to executing a quality control test;
receiving continually, at the controller, a plurality of data values related to the diagnostic analyzer before a next quality control test;
analyzing, with a decision module executing in the controller, the quality control test result and the data values related to the diagnostic analyzer; and
sending, from the controller to a user interface, a message indicating that the diagnostic analyzer is operating acceptably now but subsequently may not continue to do so based on the analyzing by the decision module indicating that the quality control test result is satisfactory and that at least one of the data values lies between an acceptable range and an unacceptable range;
wherein the plurality of data values related to the diagnostic analyzer comprise one or more of:
degree of water ionization;
refrigerated storage temperature reading;
reagent lot number;
reagent lot expiration date; and
onboard stability expiration date.

13. A quality control apparatus, comprising:
a diagnostic analyzer configured to perform one or more tests on biological specimens;
a controller in electronic communication with the diagnostic analyzer, the controller including:
a communication interface configured to receive:
a quality control test result from the diagnostic analyzer in response to the diagnostic analyzer executing a quality control test, and
data values related to the diagnostic analyzer, each data value associated with a first set or range of one or more values indicating acceptable analyzer operation and a second set or range of one or more values indicating unacceptable analyzer operation; and
a decision module configured and operable to analyze the quality control test result and the data values related to the diagnostic analyzer to determine whether the quality control test result corresponds with an expected quality control test result and whether each of the data values corresponds with its associated first set or range of one or more values or its associated second set or range of one or more values; and
a user interface coupled to the controller to communicate a message indicating that the diagnostic analyzer is operating acceptably now and analyzer results received from the diagnostic analyzer are valid but the diagnostic analyzer subsequently may not continue to operate acceptably and subsequent analyzer results may not be valid in response to the decision module determining that the quality control test result corresponds with the expected quality control test result and at least one of the data values is between the first and second sets or ranges of one or more values associated with that at least one of the data values.

14. The quality control apparatus of claim 13, wherein the decision module comprises an artificial intelligence-driven model trained to identify patterns in the data values related to the diagnostic analyzer that indicate subsequent unacceptable diagnostic analyzer operation.

15. The quality control apparatus of claim 13, further comprising one or more sensors coupled to the controller and the diagnostic analyzer, the one or more sensors configured to provide the data values related to the diagnostic analyzer.

16. The quality control apparatus of claim 13, wherein the data values related to the diagnostic analyzer comprise one or more of:
a sequence, number, or type of tests previously performed by the diagnostic analyzer;
internal temperature reading of the diagnostic analyzer;
internal vibration level of the diagnostic analyzer;
humidity level; and
atmospheric pressure reading.

17. The quality control apparatus of claim 13, wherein the data values related to the diagnostic analyzer comprise one or more of:
degree of water ionization;
refrigerated storage temperature reading;
reagent lot number;
reagent lot expiration date; and
onboard stability expiration date.

18. The quality control apparatus of claim 13, further comprising quality control sample specimens to be tested on the diagnostic analyzer, the quality control sample specimens having expected results from testing on the diagnostic analyzer.

19. The quality control apparatus of claim 13, wherein the decision module is configured and operable to predict a time frame during which operation of the diagnostic analyzer becomes unacceptable.

20. The quality control apparatus of claim 13, wherein the decision module is configured and operable to analyze the data values related to the diagnostic analyzer with previously stored data related to the diagnostic analyzer to predict subsequent unacceptable diagnostic analyzer operation.

21. The quality control apparatus of claim 13, wherein the user interface includes a display device.

22. The quality control apparatus of claim 13, wherein the user interface includes an audible warning device activated in response to receiving the message indicating that the diagnostic analyzer is operating acceptably now and analyzer results received from the diagnostic analyzer are valid but the diagnostic analyzer subsequently may not continue to operate acceptably and subsequent analyzer results may not be valid.

* * * * *